United States Patent
Ninomiya et al.

(10) Patent No.: US 9,993,154 B2
(45) Date of Patent: Jun. 12, 2018

(54) EYE GAZE DETECTION SUPPORTING DEVICE AND EYE GAZE DETECTION SUPPORTING METHOD

(71) Applicant: JVC KENWOOD Corporation, Yokohama-shi, Kanagawa (JP)

(72) Inventors: Masaru Ninomiya, Yokohama (JP); Katsuyuki Shudo, Yokohama (JP); Shuji Hakoshima, Yokohama (JP)

(73) Assignee: JVC KENWOOD Corporation, Kanagawa (JP)

( * ) Notice: Subject to any disclaimer, the term of this patent is extended or adjusted under 35 U.S.C. 154(b) by 41 days.

(21) Appl. No.: 15/160,058

(22) Filed: May 20, 2016

(65) Prior Publication Data

US 2016/0262614 A1    Sep. 15, 2016

Related U.S. Application Data

(63) Continuation of application No. PCT/JP2014/081123, filed on Nov. 25, 2014.

(30) Foreign Application Priority Data

Nov. 28, 2013  (JP) .................................. 2013-246725
May 29, 2014   (JP) .................................. 2014-111699

(51) Int. Cl.
*A61B 3/14*     (2006.01)
*A61B 3/113*    (2006.01)
(Continued)

(52) U.S. Cl.
CPC ............ *A61B 3/113* (2013.01); *A61B 3/0008* (2013.01); *A61B 3/0025* (2013.01);
(Continued)

(58) Field of Classification Search
CPC ... A61B 3/0008; A61B 3/0025; A61B 3/0041; A61B 3/14; A61B 3/113; G06K 9/00604;
(Continued)

(56) References Cited

U.S. PATENT DOCUMENTS 7,747,068 B1 *  6/2010  Smyth .................... G03B 17/00
                                                      382/154
7,771,049 B2 *  8/2010  Knaan .................... A61B 3/113
                                                      351/206
(Continued)

FOREIGN PATENT DOCUMENTS

EP    2467053    6/2012
EP    2965689    1/2016
(Continued)

OTHER PUBLICATIONS

International Search Report for International Patent Application No. PCT/JP2014/081123 dated Jan. 13, 2015, 5 pages.
(Continued)

*Primary Examiner* — Mustak Choudhury
(74) *Attorney, Agent, or Firm* — Amin, Turocy & Watson LLP

(57) ABSTRACT

An eye gaze detection supporting device includes an illuminator including a light source that performs irradiation with light, a plurality of imaging units, position detectors that detect a first position indicating a center of a pupil and a second position indicating a center of corneal reflection, from an image of an eye ball of a subject irradiated with light by the illuminator, and captured by the imaging units, and a calculator that calculates a fourth position indicating a curvature center of a cornea, based on a position of the light source, a third position on a display, the first position, and the second position.

4 Claims, 12 Drawing Sheets

(51) Int. Cl.
  *A61B 3/00* (2006.01)
  *A61B 3/107* (2006.01)

(52) U.S. Cl.
  CPC ............ *A61B 3/0041* (2013.01); *A61B 3/107* (2013.01); *A61B 3/14* (2013.01)

(58) Field of Classification Search
  CPC ...... G06K 9/0061; G03B 17/00; G06T 7/514; G06T 7/73
  USPC ............ 351/206–212, 218; 382/154; 396/51; 345/156
  See application file for complete search history.

(56) References Cited

U.S. PATENT DOCUMENTS

| | | | |
|---|---|---|---|
| 2003/0098954 A1* | 5/2003 | Amir | ............ A61B 3/113 351/210 |
| 2003/0123027 A1* | 7/2003 | Amir | ............ G06K 9/00604 351/209 |
| 2014/0055342 A1* | 2/2014 | Kamimura | ............ G06F 3/013 345/156 |

FOREIGN PATENT DOCUMENTS

| | | |
|---|---|---|
| EP | 3015075 | 5/2016 |
| JP | 02-134130 | 5/1990 |
| JP | 2007-209384 | 8/2007 |
| JP | 2014-195641 | 10/2014 |

OTHER PUBLICATIONS

Written Opinion for International Patent Application No. PCT/JP2014/081123 dated Jan. 13, 2015, 4 pages.

Extended European Search Report for European Patent Application No. 14865795.0 dated Nov. 18, 2016.

* cited by examiner

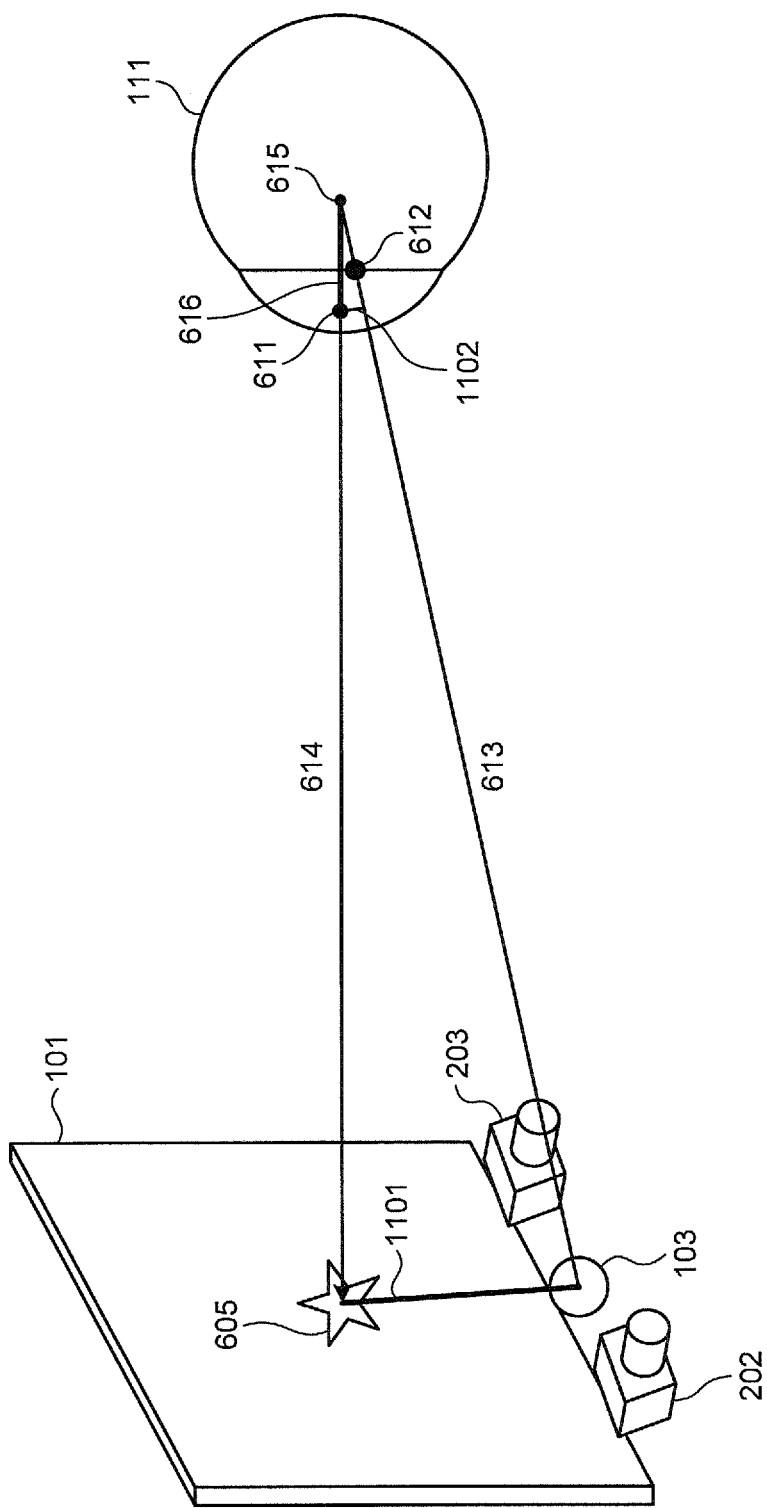

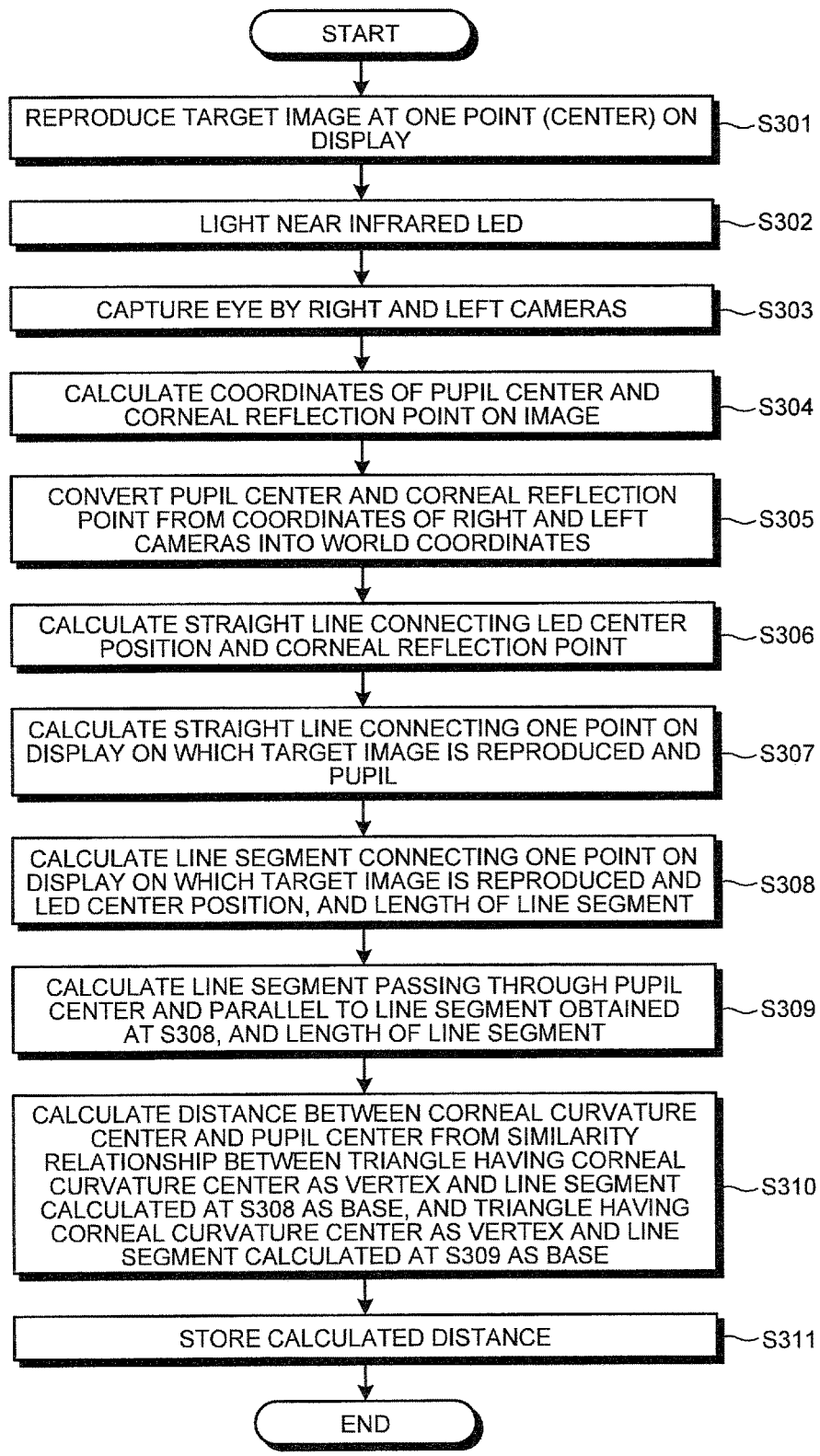

EYE GAZE DETECTION SUPPORTING DEVICE AND EYE GAZE DETECTION SUPPORTING METHOD

CROSS-REFERENCE TO RELATED APPLICATIONS

This application is a continuation of PCT international application Ser. No. PCT/JP2014/081123 filed on Nov. 25, 2014 which designates the United States, incorporated herein by reference, and which claims the benefit of priority from Japanese Patent Application No. 2013-246725, filed on Nov. 28, 2013 and Japanese Patent Application No. 2014-111699, filed on May 29, 2014, incorporated herein by reference.

BACKGROUND OF THE INVENTION

1. Field of the Invention

The present invention relates to an eye gaze detection supporting device and an eye gaze detection supporting method.

2. Description of the Related Art

Eye gaze detection devices that detect a position that an operator or a subject is gazing at, on an observation surface such as a monitor screen, have been proposed. For example, methods that enable non-contact eye gaze detection are known, in which an eye gaze direction is reliably detected without attachment of any device to the face of the subject. In these methods, eye ball reflection of light irradiated from a light source is detected, a pupil center and a corneal curvature center are calculated, and a straight line that connects the pupil center and the corneal curvature center is detected as the eye gaze. In many of the methods, the eye ball reflection of light irradiated from two or more light sources is detected, and the eye gaze is calculated.

In the method of Patent Literature 1 (Japanese Patent No. 2739331), two cameras and two light sources are used, two corneal reflection points are detected in one eye ball, the corneal curvature center is calculated from the two corneal reflection points, and the eye gaze is detected from a positional relationship between the corneal curvature center and the pupil center. In the method of Patent Literature 2 (Japanese Patent No. 4824420), one camera and two light sources are used, the corneal curvature center is calculated from a line of intersection of planes respectively including the two corneal reflection points, and the eye gaze is detected from a positional relationship between the corneal curvature center and the pupil center.

However, the above-described methods of Patent Literatures have problems that a device configuration becomes complicated, and the size of the device becomes large. For example, when two light sources are used, two reflection points corresponding to the respective light sources are separately detected. Therefore, the distance between the two light sources needs to be separated by a predetermined distance or more. This is because, if the distance between the light sources is close, the two reflection points overlap with each other and separation becomes difficult.

Therefore, there is a need for an eye gaze detection supporting device and an eye gaze detection supporting method that can simplify the device configuration.

SUMMARY OF THE INVENTION

It is an object of the present invention to at least partially solve the problems in the conventional technology.

An eye gaze detection supporting device according to the present invention includes an illuminator including a light source that performs irradiation with light, a plurality of imaging units, a position detector configured to detect a first position indicating a center of a pupil and a second position indicating a center of corneal reflection, from an image of an eye ball of a subject irradiated with the light by the illuminator, and captured by the imaging units, and a calculator configured to calculate a fourth position indicating a curvature center of a cornea, based on a position of the light source, a third position on a display, the first position, and the second position.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 is a diagram for describing calculation processing of a modification.

FIG. 12 is a flowchart illustrating an example of calculation processing of the modification.

DETAILED DESCRIPTION OF THE PREFERRED EMBODIMENTS

Hereinafter, embodiments of an eye gaze detection supporting device and an eye gaze detection supporting method according to the present invention will be described in detail based on the drawings. Note that the invention is not limited by these embodiments. Further, hereinafter, an example of using the eye gaze detection supporting device, as a diagnosis supporting device that supports diagnosis of developmental disorder and the like, using an eye gaze detection result, will be described. An applicable device is not limited to the diagnosis supporting device.

An eye gaze detection supporting device (diagnosis supporting device) of the present embodiment detects an eye gaze, using an illuminator installed in one place. Further, the eye gaze detection supporting device (diagnosis supporting device) of the present embodiment calculates a corneal curvature center position high accurately, using a result of measurement obtained by causing a subject to gaze at one point, before detection of the eye gaze.

Note that the illuminator is an element that includes a light source and can irradiate an eye ball of the subject with light. The light source is an element that emits light, such as a light emitting diode (LED). The light source may be configured from one LED, or may be configured such that a plurality of LEDs is combined and is arranged at one place. Hereinafter, "light source" may be used as a term that indicates the illuminator.

Figure 1:
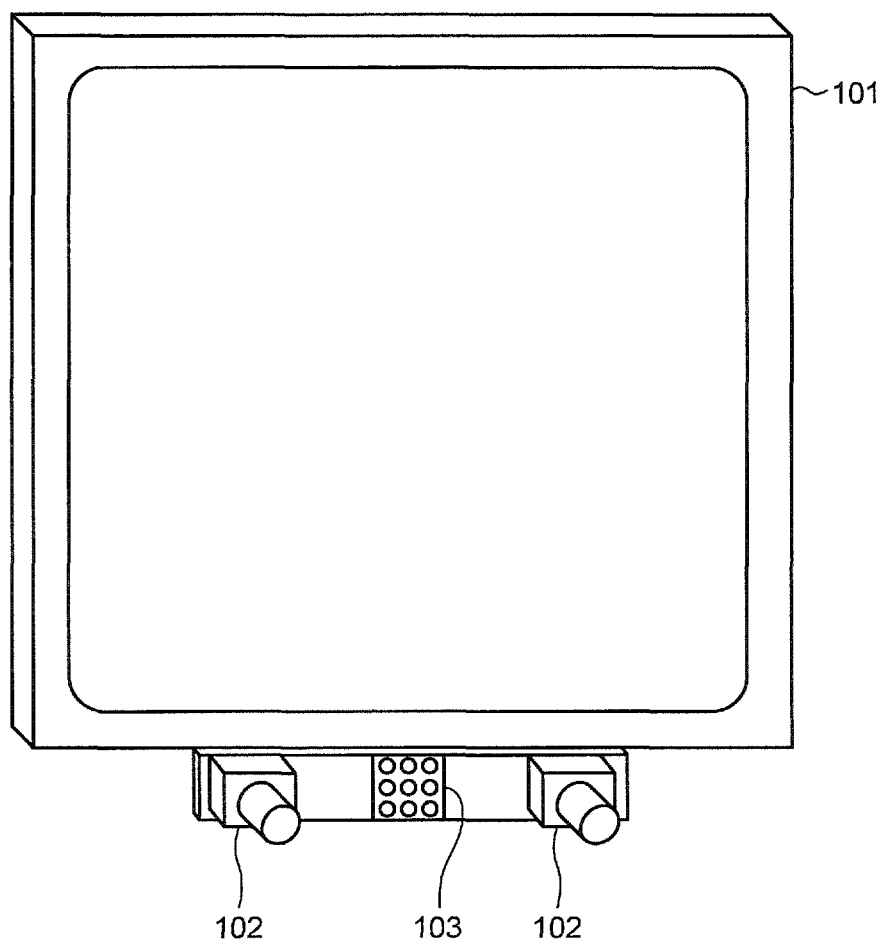
FIG. 1 is a diagram illustrating an example of arrangement of a display, a stereo camera, an infrared light source of the present embodiment.
Figure 2:
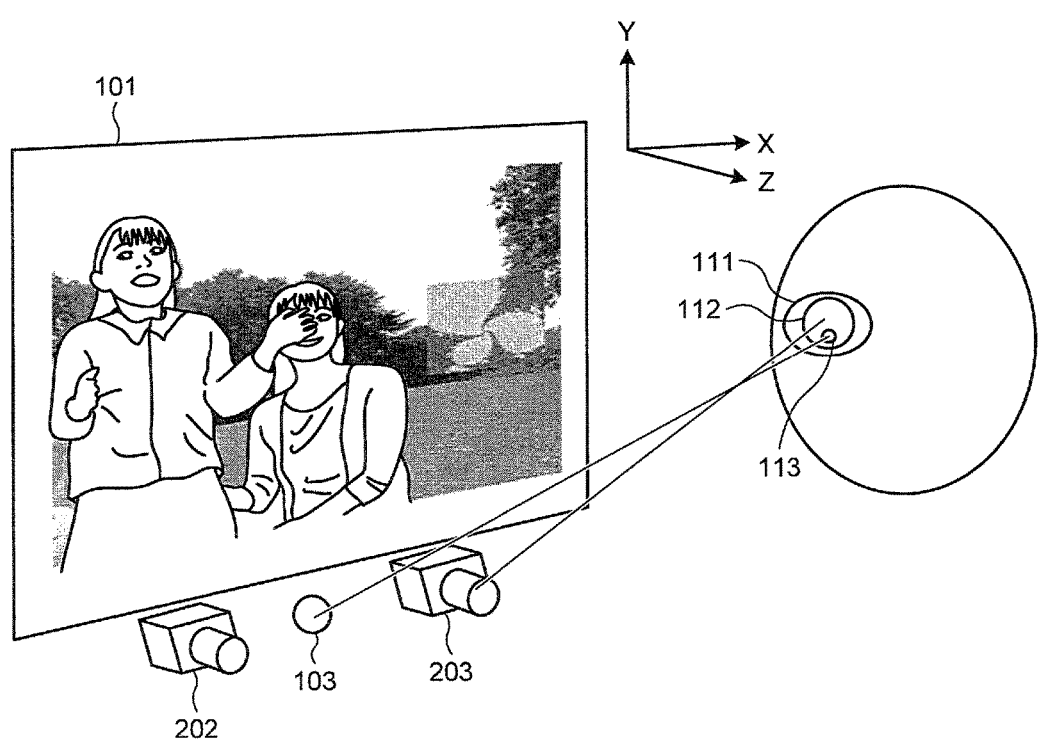
FIG. 2 is a diagram illustrating an example of arrangement of the display, the stereo camera, the infrared light source of the present embodiment, and a subject.

FIGS. 1 and 2 are diagrams illustrating an example of arrangement of a display, a stereo camera, an infrared light source of the present embodiment and a subject.

As illustrated in FIG. 1, a diagnosis supporting device of the present embodiment includes a display 101, a stereo camera 102, and an LED light source 103. The stereo camera 102 is arranged under the display 101. The LED light source 103 is arranged at a center position of two cameras included in the stereo camera 102. The LED light source 103 is, for example, a light source that irradiates the subject with a near infrared ray with a wavelength of 850 nm. FIG. 1 illustrates an example in which the LED light source 103 (illuminator) is configured from nine LEDs. Note that, in the stereo camera 102, a lens that can transmit near infrared light with a wavelength of 850 nm is used.

As illustrated in FIG. 2, the stereo camera 102 includes a right camera 202 and a left camera 203. The LED light source 103 irradiates an eye ball 111 of the subject with the near infrared light. In an image obtained by the stereo camera 102, a pupil 112 is reflected at low luminance and becomes dark, and corneal reflection 113 caused in the eye ball 111, as a virtual image, is reflected at high luminance and becomes bright. Therefore, positions of the pupil 112 and the corneal reflection 113 on the image can be obtained by the two cameras (the right camera 202 and the left camera 203).

Further, three-dimensional world coordinate values of positions of the pupil 112 and the corneal reflection 113 are calculated from the positions of the pupil 112 and the corneal reflection 113 obtained by the two cameras. In the present embodiment, as the three-dimensional world coordinates, a coordinate in an up and down direction is a Y coordinate (the up direction is +), a coordinate in a transverse direction is an X coordinate (the right direction is +), and a coordinate in a depth direction is a Z coordinate (the front side is +), where a middle position on the screen of the display 101 is the origin.

Figure 3:
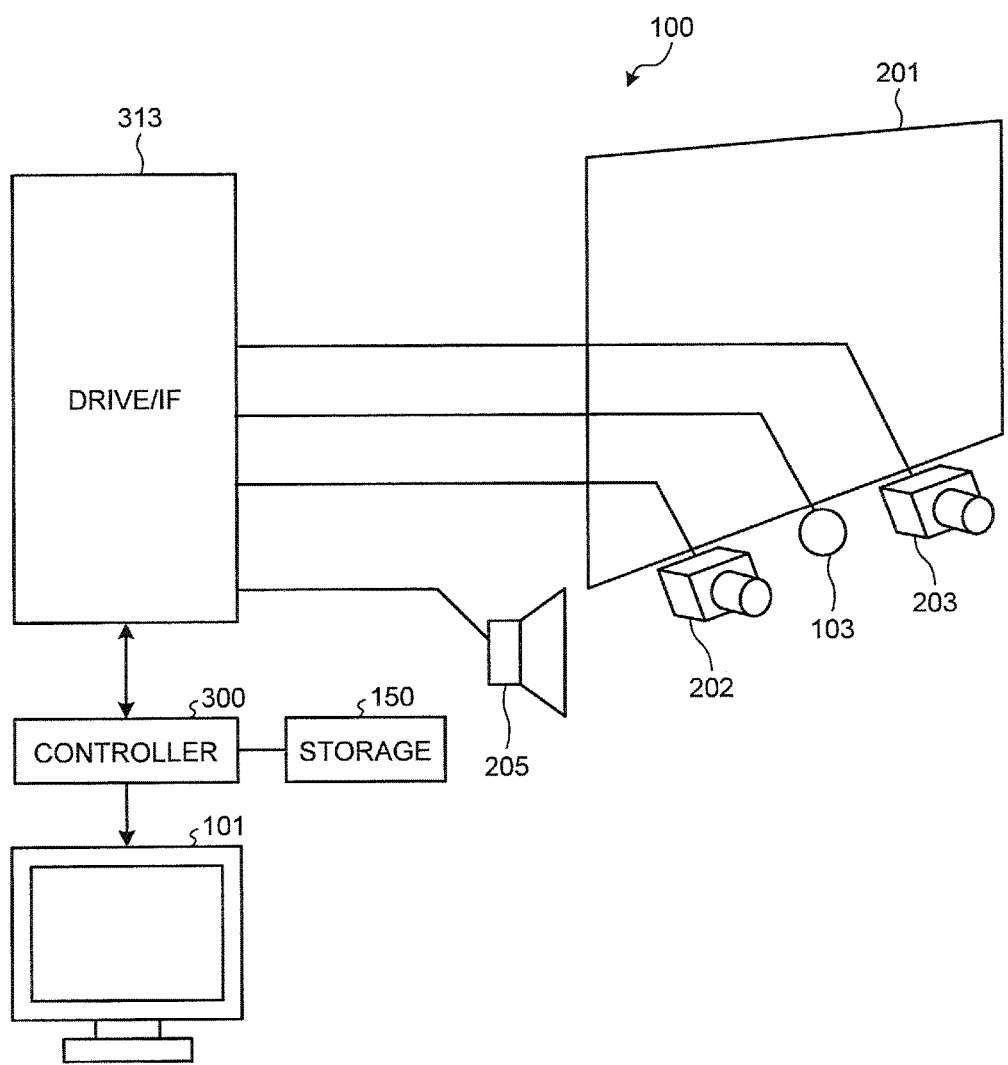
FIG. 3 is a diagram illustrating an outline of functions of a diagnosis supporting device.

FIG. 3 is a diagram illustrating an outline of functions of a diagnosis supporting device 100. FIG. 3 illustrates a part of the configurations illustrated in FIGS. 1 and 2, and configurations used for driving the aforementioned configurations. As illustrated in FIG. 3, the diagnosis supporting device 100 includes the right camera 202, the left camera 203, the LED light source 103, a speaker 205, a drive/IF (interface) 313, a controller 300, a storage 150, and the display 101. In FIG. 3, a positional relationship between a display screen 201, and the right camera 202 and the left camera 203 is illustrated in an easily understandable manner. The display screen 201 is a screen displayed in the display 101. Note that the driver and the IF may be integrated or separated.

The speaker 205 functions as an audio output unit that outputs an audio and the like for prompting the subject to pay attention, at the time of calibration and the like.

The drive/IF 313 drives units included in the stereo camera 102. Further, the drive/IF 313 serves as an interface between the units included in the stereo camera 102, and the controller 300.

The controller 300 can be realized by a computer that includes a control device such as a central processing unit (CPU), a storage device such as read only memory (ROM) and random access memory (RAM), a communication I/F that is connected with a network and performs communication, and a bus that connects the units.

The storage 150 stores various types of information such as a control program, a measurement result, and a diagnosis support result. The storage 150 stores an image to be displayed in the display 101, and the like. The display 101 displays various types of information such as an object image for diagnosis, and the like.

Figure 4:
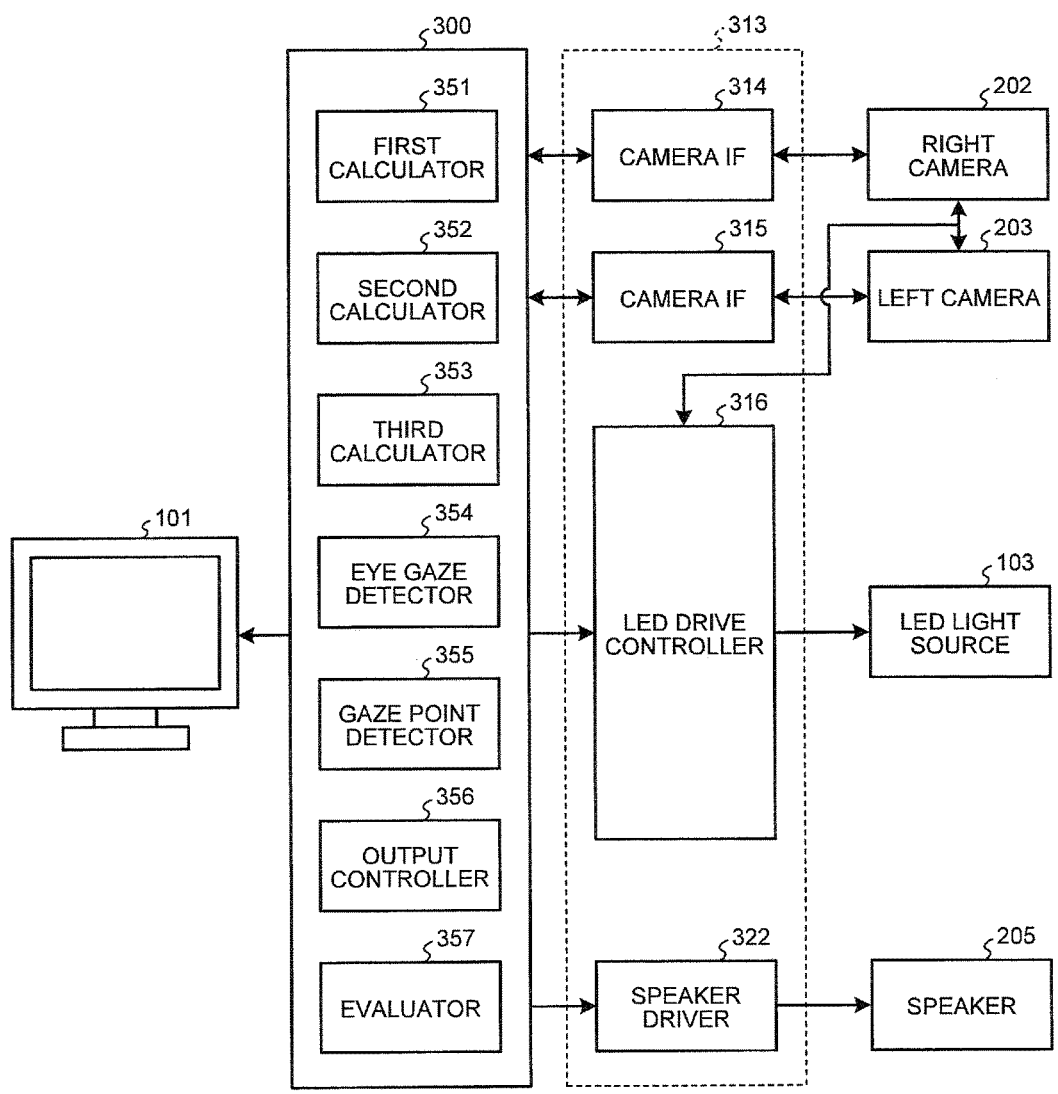
FIG. 4 is a block diagram illustrating an example of detailed functions of respective units illustrated in FIG. 3.

FIG. 4 is a block diagram illustrating an example of detailed functions of the respective units illustrated in FIG. 3. As illustrated in FIG. 4, the display 101 and the drive/IF 313 are connected to the controller 300. The drive/IF 313 includes camera IFs 314 and 315, an LED drive controller 316, and a speaker driver 322.

The right camera 202 and the left camera 203 are connected to the drive/IF 313 through the camera IFs 314 and 315, respectively. The drive/IF 313 drives these cameras to capture the subject.

The speaker driver 322 drives the speaker 205. Note that the diagnosis supporting device 100 may include an interface (printer IF) for being connected with a printer as a print unit. Further, the printer may be included inside the diagnosis supporting device 100.

The controller 300 controls the entire diagnosis supporting device 100. The controller 300 includes a first calculator 351, a second calculator 352, a third calculator 353, an eye gaze detector 354, a gaze point detector 355, an output controller 356, and an evaluator 357. Note that, as the eye gaze detection supporting device, the controller 300 may just include at least the first calculator 351, the second calculator 352, the third calculator 353, and the eye gaze detector 354.

The elements (the first calculator 351, the second calculator 352, the third calculator 353, the eye gaze detector 354, the gaze point detector 355, the output controller 356, and the evaluator 357) included in the controller 300 may be realized by software (programs), may be realized by a hardware circuit, or may be realized by use of the software and the hardware circuit together.

When the elements are realized by the programs, the programs are recorded in a computer-readable recording medium such as a compact disk read only memory (CD-ROM), a flexible disk (FD), a compact disk recordable (CD-R), or a digital versatile disk (DVD) in a file in an installable format or in an executable format, and provided as a computer program product. The programs may be stored on a computer connected to a network such as the Internet, and provided by being downloaded through the network. Further, the programs may be provided or distributed through the network such as the Internet. Further, the programs may be provided by being incorporated in ROM or the like in advance.

The first calculator 351 calculates a position (first position) of a pupil center that indicates a center of a pupil, from an image of an eye ball captured by the stereo camera 102. The second calculator 352 calculates a position (second position) of a corneal reflection center that indicates a center of corneal reflection, from the captured image of an eye ball. The first calculator 351 and the second calculator 352 correspond to a position detector that detects the first position that indicates the center of the pupil, and the second position that indicates the center of the corneal reflection.

The third calculator 353 calculates a corneal curvature center (fourth position), from a straight line (first straight line) that connects the LED light source 103 and the corneal reflection center. For example, the third calculator 353 calculates a position where the distance from the corneal reflection center becomes a predetermined value, on the straight line, as the corneal curvature center. As the predetermined value, a value determined from a curvature radius value of a typical cornea or the like in advance can be used.

The curvature radius value of a cornea varies among different individuals, and thus an error may become large if the corneal curvature center is calculated using the value determined in advance. Therefore, the third calculator 353 may calculate the corneal curvature center in consideration of the individual difference. In this case, first, the third calculator 353 calculates an intersection point of a straight line (second straight line) that connects the pupil center and a target position (third position), and the straight line (first straight line) that connects the corneal reflection center and the LED light source 103, using the pupil center and the corneal reflection center calculated when the subject is caused to gaze at the target position. The third calculator 353 then calculates a distance (first distance) between the pupil center and the calculated intersection point, and stores the calculated distance in the storage 150, for example.

The target position may be any position as long as the position can be determined in advance, and three-dimensional world coordinate values can be calculated. For example, a middle position (the origin of the three-dimensional world coordinates) of the display screen 201 can be used as the target position. In this case, for example, the output controller 356 displays an image (target image) or the like that the subject is caused to gaze at, in the target position (center) on the display screen 201. Accordingly, the subject can gaze at the target position.

The target image may be any image as long as the image can draw attention from the subject. For example, an image with a varying display form such as luminance or a color, an image having different display form from other regions, or the like can be used as the target image.

Note that the target position is not limited to the center of the display screen 201, and any position can be employed. If the center of the display screen 201 is employed as the target position, the distance between the center and any end part of the display screen 201 is minimized. Therefore, for example, a measurement error at the time of detecting the eye gaze can be made smaller.

Processing up to the calculation of the distance is executed in advance before actual detection of the eye gaze is started. At the time of actual detection of the eye gaze, the third calculator 353 calculates a position where the distance from the pupil center becomes the distance calculated in advance, on the straight line that connects the LED light source 103 and the corneal reflection center, as the corneal curvature center. The third calculator 353 corresponds to a calculator that calculates the corneal curvature center (fourth position) from the position of the LED light source 103, the predetermined position (third position) that indicates the target image on the display, the position of the pupil center, and the position of the corneal reflection center.

The eye gaze detector 354 detects the eye gaze of the subject from the pupil center and the corneal curvature center. For example, the eye gaze detector 354 detects a direction from the corneal curvature center toward the pupil center, as an eye gaze direction of the subject.

The gaze point detector 355 detects a gaze point of the subject, using the detected eye gaze direction. The gaze point detector 355 detects, for example, a gaze point that is a point that the subject gazes at on the display screen 201. The gaze point detector 355 detects an intersection point of an eye gaze vector and an XY plane, which are expressed in a three-dimensional world coordinate system as illustrated in FIG. 2, as the gaze point of the subject.

The output controller 356 controls output of various types of information to the display 101, the speaker 205, and the like. For example, the output controller 356 outputs the target image to the target position on the display 101. Further, the output controller 356 controls output to the display 101, such as a diagnosis image, an evaluation result by the evaluator 357, and the like.

The diagnosis image may just be an image according to evaluation processing based on an eye gaze (gaze point) detection result. For example, when a developmental disorder is diagnosed, a diagnosis image that includes an image (a geometrical pattern picture or the like) preferred by the subject with the developmental disorder, and another image (a picture of a person, or the like) may be used.

The evaluator 357 performs evaluation processing based on the diagnosis image, and the gaze point detected by the gaze point detector 355. For example, when the developmental disorder is diagnosed, the evaluator 357 analyzes the diagnosis image and the gaze point, and evaluates whether the subject with the developmental disorder has gazed at the image that the subject prefers.

Figure 5:
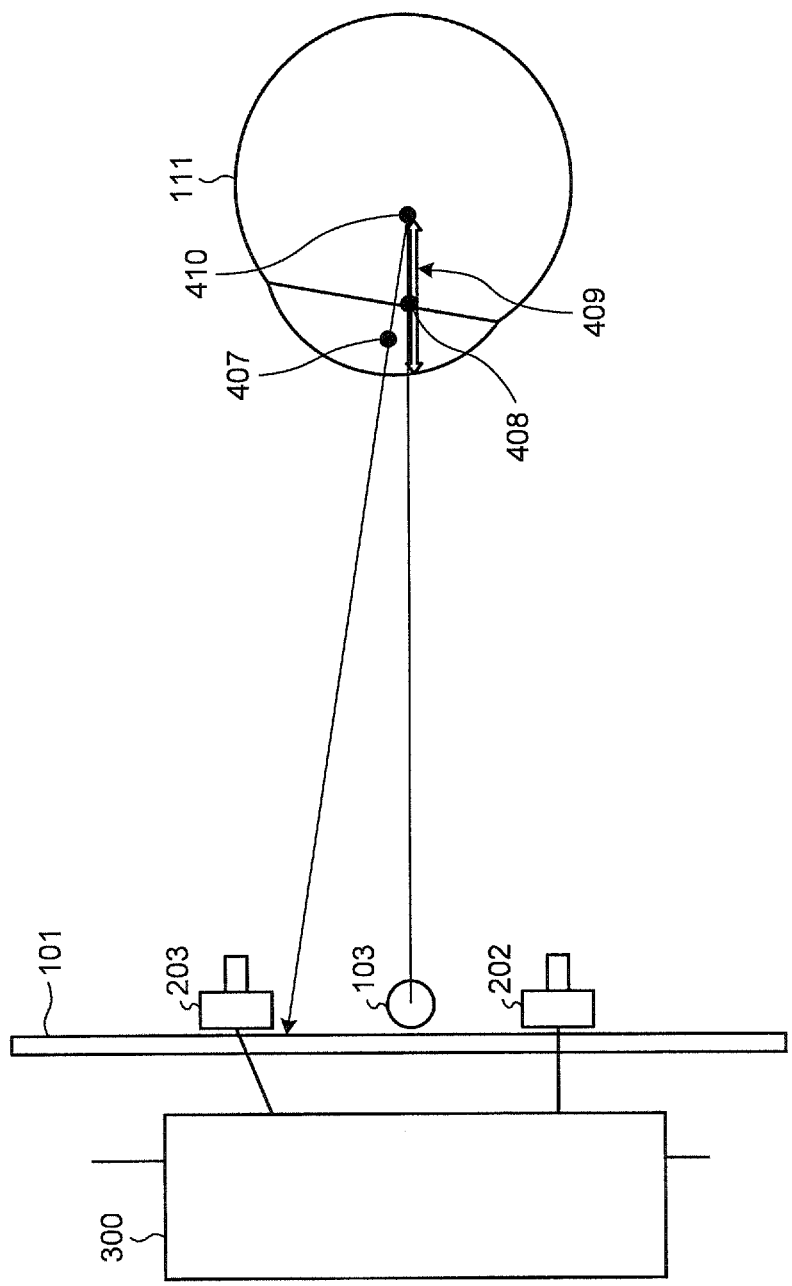
FIG. 5 is a diagram illustrating an outline of processing executed by the diagnosis supporting device of the present embodiment.

FIG. 5 is a diagram for describing an outline of processing executed by the diagnosis supporting device 100 of the present embodiment. Elements described in FIGS. 1 to 4 are denoted with the same reference signs, and descriptions are omitted.

A pupil center 407 and a corneal reflection center 408 respectively indicate the center of the pupil and the center of a corneal reflection point detected when the LED light source 103 is lighted. A cornea curvature radius 409 indicates the distance from a surface of the cornea to a corneal curvature center 410.

Figure 6:
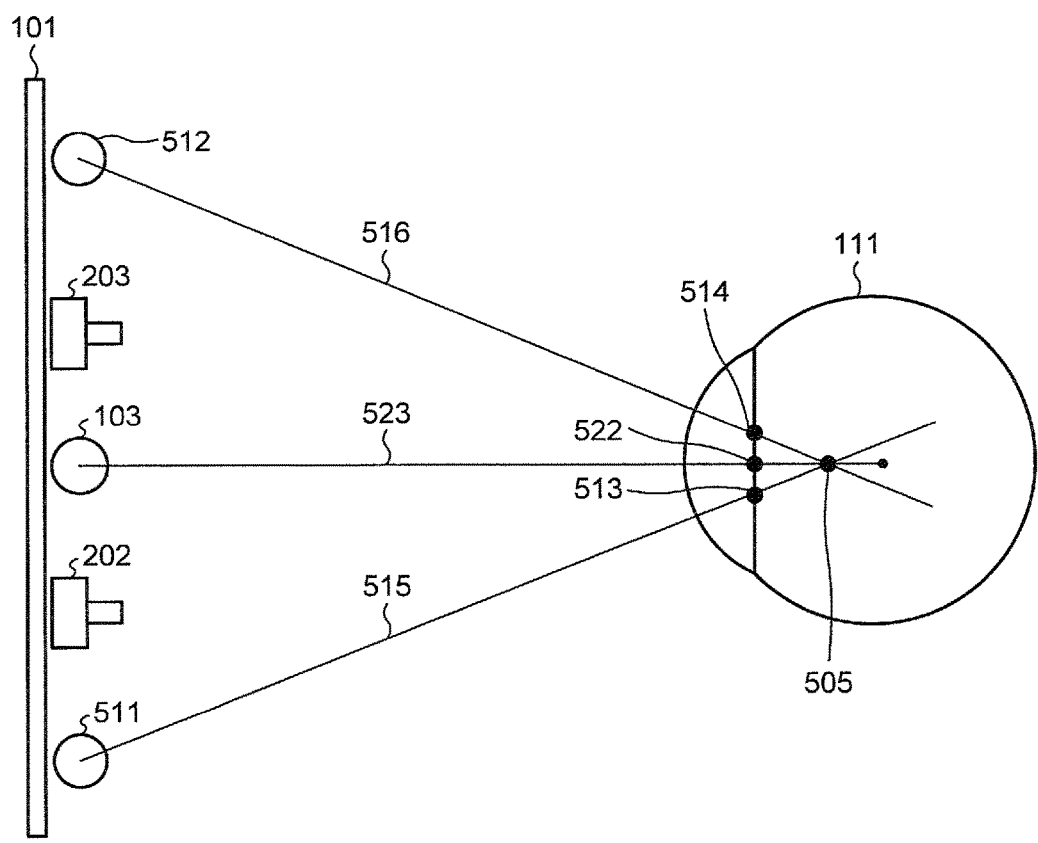
FIG. 6 is an explanatory diagram illustrating a difference between a method of using two light sources and the present embodiment using one light source.

FIG. 6 is an explanatory diagram illustrating a difference between a method using two light sources (illuminators) (hereinafter, referred to as method A), and the present embodiment using one light source (illuminator). Elements described in FIGS. 1 to 4 are denoted with the same reference signs, and descriptions are omitted.

The method A uses two LED light sources 511 and 512, in place of the LED light source 103. In the method A, an intersection point of a straight line 515 that connects a corneal reflection center 513 and the LED light source 511 of when the LED light source 511 irradiates the subject with light, and a straight line 516 that connects a corneal reflection center 514 and the LED light source 512 of when the LED light source 512 irradiates the subject with light is calculated. This intersection point serves as a corneal curvature center 505.

In contrast, in the present embodiment, a straight line 523 that connects a corneal reflection center 522 and the LED light source 103 of when the LED light source 103 irradiates the subject with light is considered. The straight line 523 passes through the corneal curvature center 505. Further, the curvature radius of a cornea is known to have a small influence due to the individual difference and have a nearly fixed value. According to this fact, the corneal curvature center of when the LED light source 103 irradiates the subject with light exists on the straight line 523, and can be calculated using a typical curvature radius value.

However, when the gaze point is calculated using the position of the corneal curvature center obtained using the typical curvature radius value, the gaze point position is deviated from an original position due to the individual difference of the eye ball, and an accurate gaze point position may not be able to be detected.

Figure 7:
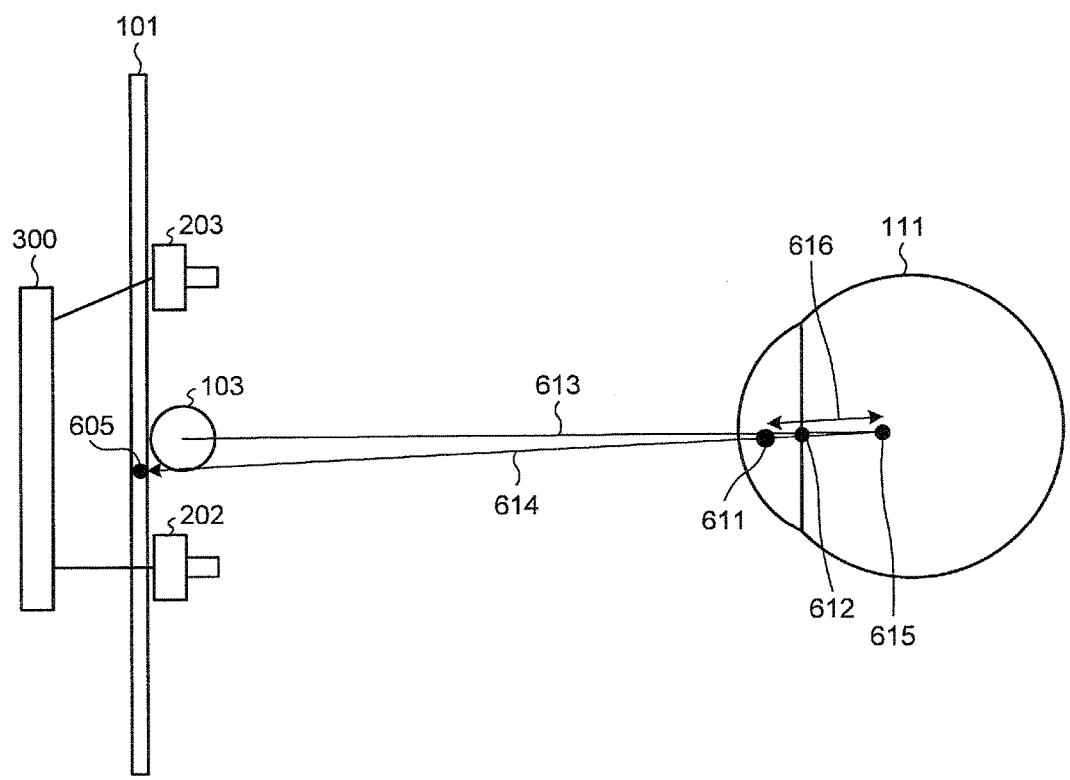
FIG. 7 is a diagram for describing calculation processing of calculating a distance between a pupil center position and a corneal curvature center position.

FIG. 7 is a diagram for describing calculation processing of calculating a corneal curvature center position, and the distance between a pupil center position and the corneal curvature center position, before the gaze point detection (eye gaze detection) is performed. Elements described in FIGS. 1 to 4 are denoted with the same reference signs, and descriptions are omitted.

A target position 605 is a position for causing the subject to gaze at, by outputting of a target image or the like to one point on the display 101. In the present embodiment, the target position 605 is a middle position on the screen of the display 101. A straight line 613 is a straight line that connects the LED light source 103 and a corneal reflection center 612. A straight line 614 is a straight line that connects the target position 605 (gaze point) that the subject gazes at and a pupil center 611. A corneal curvature center 615 is an intersection point of the straight line 613 and the straight line 614. The third calculator 353 calculates and stores a distance 616 between the pupil center 611 and the corneal curvature center 615.

Figure 8:
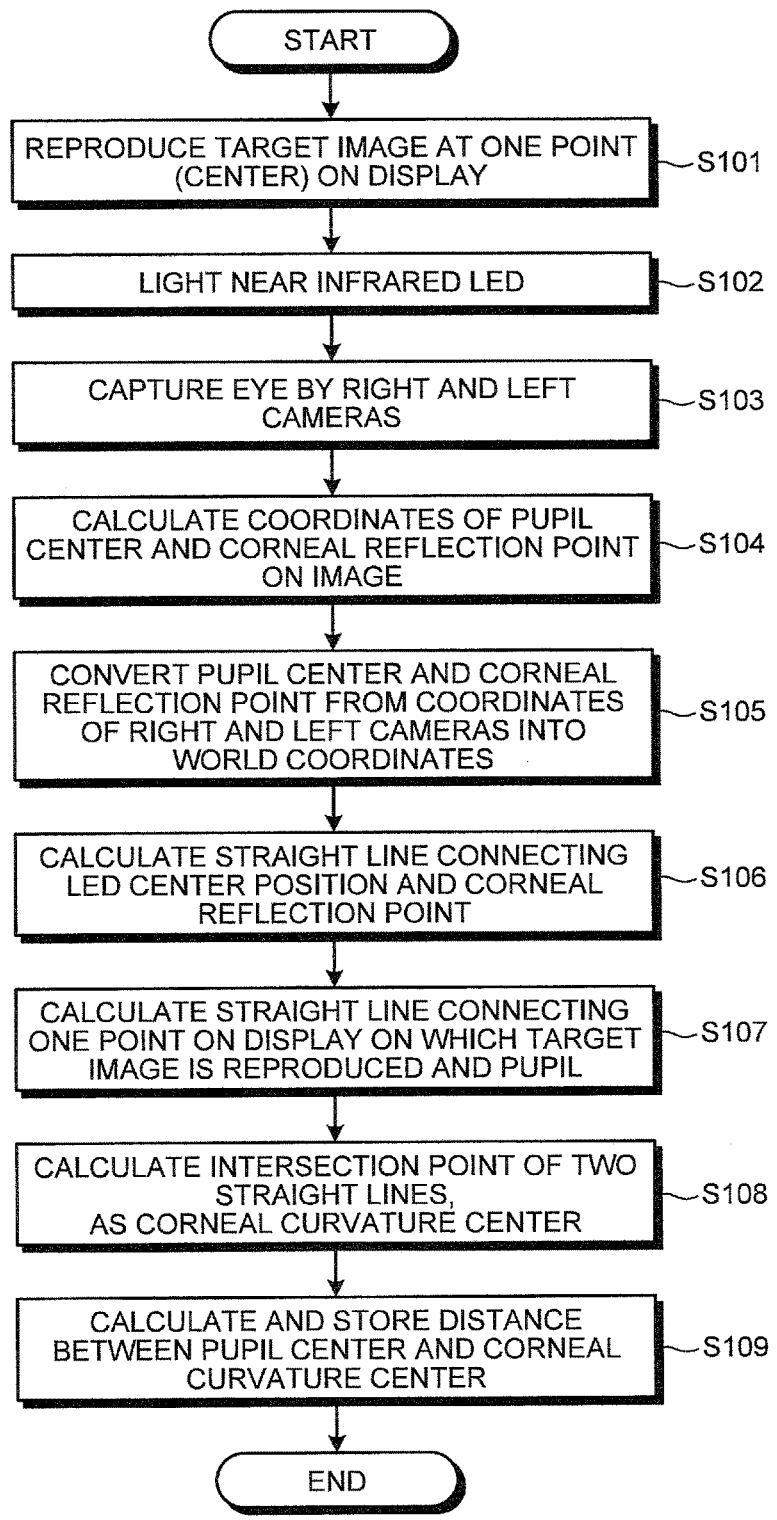
FIG. 8 is a flowchart illustrating an example of the calculation processing of the present embodiment.

FIG. 8 is a flowchart illustrating an example of calculation processing in the present embodiment.

First, the output controller 356 reproduces the target image at one point on the screen of the display 101 (step S101), and prompts the subject to gaze at the one point. Next, the controller 300 lights the LED light source 103 toward an eye of the subject, using the LED drive controller 316 (step S102). The controller 300 captures the eye of the subject by the right and left cameras (the right camera 202 and the left camera 203) (step S103).

By the irradiation of the LED light source 103, a pupil part is detected as a dark part (dark pupil). Further, as reflection of the LED irradiation, a virtual image of the corneal reflection occurs, and a corneal reflection point (corneal reflection center) is detected as a bright part. That is, the first calculator 351 detects the pupil part from the captured image, and calculates coordinates that indicate the position of the pupil center. The first calculator 351 detects a region having predetermined brightness or less including the darkest part in a fixed region including, for example, the eye, as the pupil part. Further, the first calculator 351 detects a region having predetermined brightness or more including the brightest part, as the corneal reflection. Further, the second calculator 352 detects a corneal reflection part from the captured image, and calculates coordinates that indicate the position of the corneal reflection center. Note that the first calculator 351 and the second calculator 352 calculate coordinate values of respective two images obtained by the right and left cameras (step S104).

Note that the right and left cameras are subjected to camera calibration by a stereo calibration method in advance in order to acquire the three-dimensional world coordinates, and a conversion parameter is calculated. As the stereo calibration method, any conventionally used method can be applied, such as a method using the Tsai's camera calibration theory or the like.

The first calculator 351 and the second calculator 352 convert the coordinates of the right and left cameras into three-dimensional world coordinates of the pupil center and the corneal reflection center, using the conversion parameter (step S105). The third calculator 353 obtains a straight line that connects the obtained world coordinates of the corneal reflection center, and the world coordinates of the center position of the LED light source 103 (step S106). Next, the third calculator 353 calculates a straight line that connects world coordinates of a center of the target image displayed at one point on the screen of the display 101, and the world coordinates of the pupil center (step S107). The third calculator 353 obtains an intersection point of the straight line calculated at step S106 and the straight line calculated at step S107, and employs the intersection point as the corneal curvature center (step S108). The third calculator 353 calculates the distance between the pupil center and the corneal curvature center of this time, and stores the calculated distance in the storage 150 or the like (step S109). The stored distance is used to calculate the corneal curvature center at a subsequent time of detecting the gaze point (eye gaze).

The distance between the pupil center and the corneal curvature center of when the subject gazes at the one point on the display 101 in the calculation processing is constantly maintained within a range of detecting the gaze point in the display 101. The distance between the pupil center and the corneal curvature center may be obtained from an average of entire values calculated during the reproduction of the target image, or may be obtained from an average of values of several times, of values calculated during the reproduction.

Figure 9:
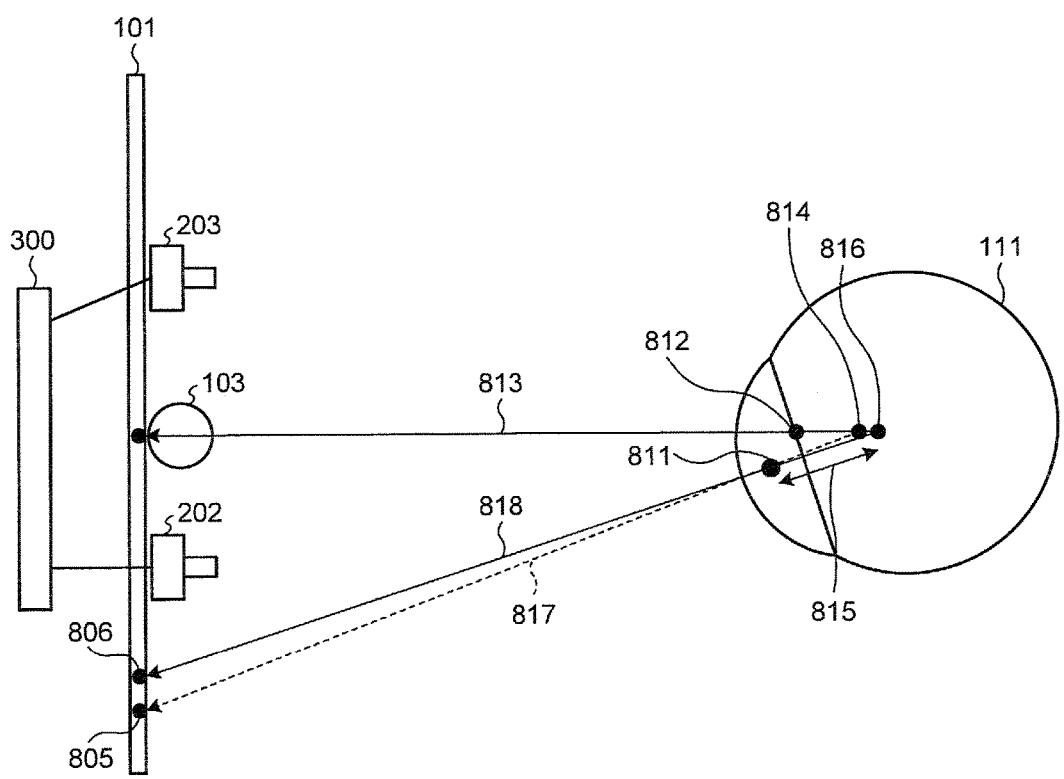
FIG. 9 is a diagram illustrating a method of calculating a corneal curvature center position using a distance obtained in advance.

FIG. 9 is a diagram illustrating a method of calculating a position of a corrected corneal curvature center, using the distance between the pupil center and the corneal curvature center obtained in advance, when the gaze point is detected. A gaze point 805 indicates the gaze point obtained from the corneal curvature center calculated using the typical curvature radius value. A gaze point 806 indicates the gaze point obtained from the corneal curvature center calculated using the distance obtained in advance.

A pupil center 811 and a corneal reflection center 812 respectively indicate the position of the pupil center calculated at the time of detecting the gaze point, and the position of the corneal reflection center. A straight line 813 is a straight line that connects the LED light source 103 and the corneal reflection center 812. A corneal curvature center 814 is the position of the corneal curvature center calculated from the typical curvature radius value. A distance 815 is the distance between the pupil center and the corneal curvature center calculated in the previous calculation processing. A corneal curvature center 816 is the position of the corneal curvature center calculated using the distance obtained in advance. The corneal curvature center 816 is obtained from the facts that the corneal curvature center exists on the straight line 813, and the distance between the pupil center and the corneal curvature center is the distance 815. Accordingly, an eye gaze 817 calculated when the typical curvature radius value is used is corrected to an eye gaze 818. Further, the gaze point on the screen of the display 101 is corrected from the gaze point 805 to the gaze point 806.

Figure 10:
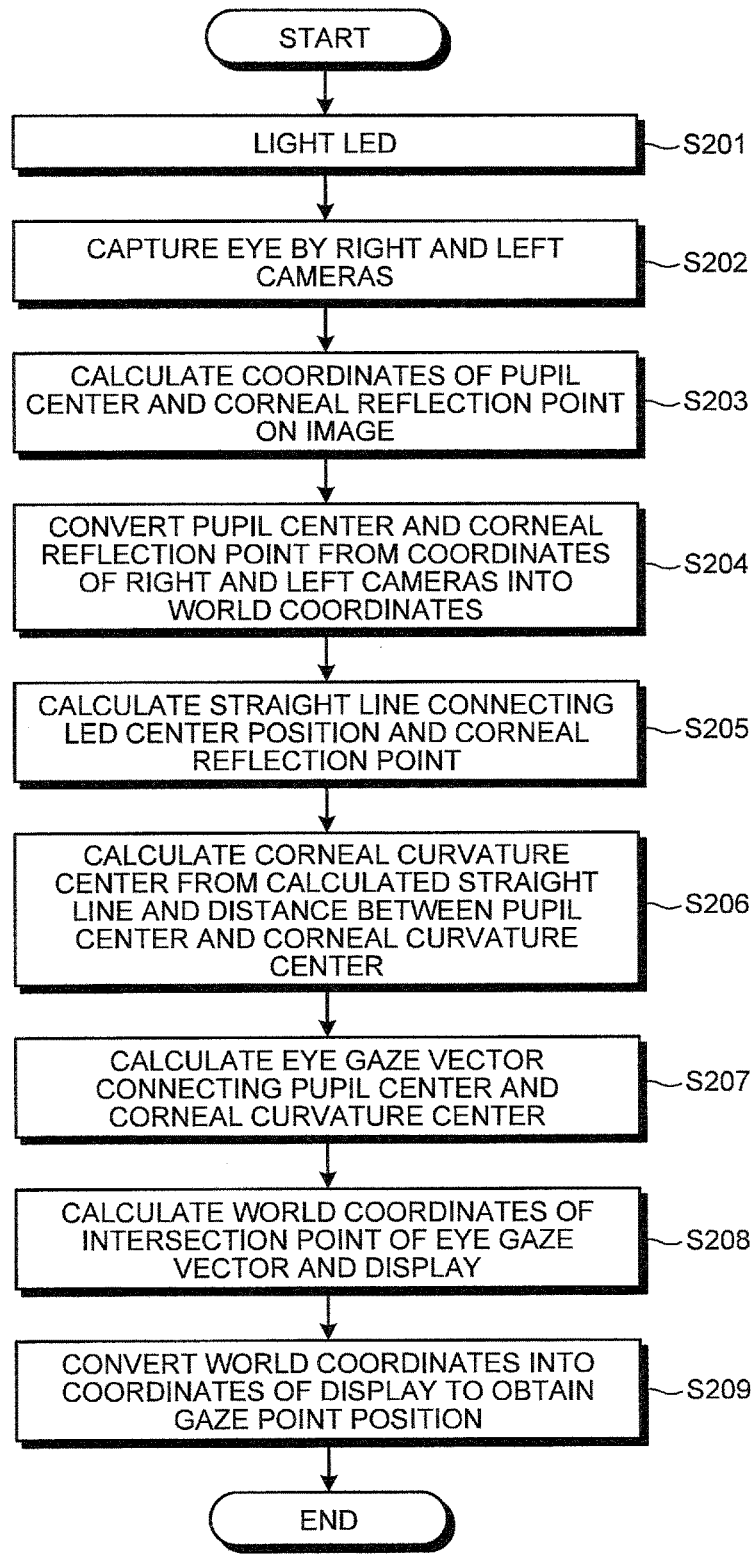
FIG. 10 is a flowchart illustrating an example of eye gaze detection processing of the present embodiment.

FIG. 10 is a flowchart illustrating an example of eye gaze detection processing of the present embodiment. For example, as processing of detecting an eye gaze in diagnosis processing using a diagnosis image, the eye gaze detection processing of FIG. 10 can be executed. In the diagnosis processing, processing of displaying a diagnosis image, evaluation processing by the evaluator 357 using the detection result of the gaze point, and the like are executed, in addition to the steps of FIG. 10.

Steps S201 to S205 are similar to steps S102 to S106 of FIG. 8, and thus descriptions are omitted.

The third calculator 353 calculates a position where the distance from the pupil center is equal to the distance obtained in the previous calculation processing, on the straight line calculated at step S205, as the corneal curvature center (step S206).

The eye gaze detector 354 obtains a vector (eye gaze vector) that connects the pupil center and the corneal curvature center (step S207). This vector indicates the eye gaze direction that the subject is looking at. The gaze point detector 355 calculates three-dimensional world coordinate values of the intersection point of the eye gaze direction and the screen of the display 101 (step S208). The values are coordinate values that express the one point on the display 101 that the subject gazes at, in the world coordinates. The gaze point detector 355 converts the obtained three-dimensional world coordinate values into coordinate values (x, y) expressed in a two-dimensional coordinate system of the display 101 (step S209). Accordingly, the gaze point on the display 101 that the subject gazes at can be calculated.

(Modification)

A method of calculating a distance between a pupil center position and a corneal curvature center position is not limited to the method described in FIGS. 7 and 8. Hereinafter, another example of calculation processing will be described using FIGS. 11 and 12.

FIG. 11 is a diagram for describing calculation processing of the present modification. Elements described in FIGS. 1 to 4, and 7 are denoted with the same reference signs, and descriptions are omitted.

A line segment 1101 is a line segment (first line segment) that connects a target position 605 and an LED light source 103. A line segment 1102 is a line segment (second line segment) that is parallel to the line segment 1101, and connects a pupil center 611 and a straight line 613. In the present modification, a distance 616 between the pupil center 611 and a corneal curvature center 615 is calculated using the line segment 1101 and the line segment 1102, and stored.

FIG. 12 is a flowchart illustrating an example of calculation processing of the present modification.

Steps S301 to S307 are similar to steps S101 to S107 of FIG. 8, and thus description is omitted.

A third calculator 353 calculates a line segment (the line segment 1101 in FIG. 11) that connects a center of a target image displayed at one point on a screen of a display 101, and a center of the LED light source 103, and calculates the length of the calculated line segment (the length is L1101) (step S308).

The third calculator 353 calculates a line segment (the line segment 1102 in FIG. 11) passing through the pupil center 611, and parallel to the line segment calculated at step S308, and calculates the length of the calculated line segment (the length is L1102) (step S309).

The third calculator 353 calculates a distance 616 between the pupil center 611 and the corneal curvature center 615 based on the fact that a triangle having the corneal curvature center 615, as a vertex, and the line segment calculated at step S308, as a base, and a triangle having the corneal curvature center 615, as a vertex, and the line segment calculated at step S309, as a base have a similarity relationship (step S310). For example, the third calculator 353 calculates the distance 616 such that a ratio of the length of the line segment 1102 to the length of the line segment 1101, and a ratio of the distance 616 to the distance between the target position 605 and the corneal curvature center 615 become equal.

The distance 616 can be calculated by the following formula (1). Note that a distance L614 is the distance from the target position 605 to the pupil center 611.

$$\text{Distance } 616 = (L614 \times L1102)/(L1101 - L1102) \tag{1}$$

The third calculator 353 stores the calculated distance 616 in a storage 150 or the like (step S311). The stored distance is used to calculate the corneal curvature center at a subsequent time of detecting a gaze point (eye gaze).

As described above, according to the present embodiment, the following effects can be obtained, for example.

(1) It is not necessary to arrange the light source (illuminator) at two places, and the eye gaze can be detected with the light source arranged at one place.

(2) The light source is arranged at one place, whereby the device can be made compact, and reduction of cost can be realized.

In short, the eye gaze detection supporting device and the eye gaze detection supporting method according to the present invention exert an effect to simplify a device configuration.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An eye gaze detection supporting device comprising:
    an illuminator including a single light source that performs irradiation with light;
    a plurality of imaging units;
    a position detector configured to
        detect a first position indicating a center of a pupil from an image of an eye ball of a subject irradiated with the light by the illuminator, and captured by the imaging units, and
        detect, from the image, a region having predetermined brightness including the brightest part as corneal reflection and detect a second position indicating a center of the corneal reflection; and
    a calculator configured to calculate a fourth position indicating a curvature center of a cornea, based on a position of the light source, the fourth position indicating the distance from the corneal reflection center becoming a predetermined value, on a straight line, a third position indicating the target image on a display, the first position, and the second position; and
    an eye gaze detector processor or circuit configured to detect an eye gaze, based on the first position and the fourth position.

2. The eye gaze detection supporting device according to claim 1, wherein
    the calculator
    calculates a first straight line connecting a position of the light source and the second position, and
    a second straight line connecting the first position and the third position, and
    calculates the fourth position existing on the first straight line, and at which a distance from the first position becomes a first distance, where
    the first distance is a distance between an intersection point of the first straight line and the second straight line, and the first position.

3. An eye gaze detection supporting device comprising:
an illuminator including a light source that performs irradiation with light:
a plurality of imaging units;
a position detector configured to detect a first position indicating a center of a pupil and a second position indicating a center of corneal reflection, from an image of an eye ball of a subject irradiated with the light by the illuminator, and captured by the imaging units; and
a calculator configured to calculate a fourth position indicating a curvature center of a cornea, based on a position of the light source, a third position on a display, the first position, and the second position, wherein
the calculator
calculates a first straight line connecting a position of the light source and the second position, and a second straight line connecting the first position and the third position,
calculates the fourth position existing on the first straight line, and at which a distance from the first position becomes a first distance, where the first distance is a distance between an intersection point of the first straight line and the second straight line, and the first position,
calculates a first line segment connecting the position of the light source and the third position, and
a second line segment parallel to the first line segment, and going from the first position to the first straight line, and
calculates the first distance where a ratio of a length of the second line segment to a length of the first line segment, and a ratio of the first distance to a distance between the third position and the fourth position become equal to detect an eye gaze, by an eye gaze detector processor or circuit.

4. An eye gaze detection supporting method comprising the steps of:
detecting a first position indicating a center of a pupil and a second position indicating a center of corneal reflection, from an image of an eye ball of a subject irradiated with light by an illuminator including a light source, and captured by a plurality of imaging units; and
calculating, by a calculator, a fourth position indicating a curvature center of a cornea, based on a position of the light source, a third position on a display, the first position, and the second position, wherein
the calculating includes the steps of
calculating, by a calculator, a first straight line connecting a position of the light source and the second position, and a second straight line connecting the first position and the third position,
calculating, by a calculator, the fourth position existing on the first straight line, and at which a distance from the first position becomes a first distance, where the first distance is a distance between an intersection point of the first straight line and the second straight line, and the first position,
calculating, by a calculator, a first line segment connecting the position of the light source and the third position, and a second line segment parallel to the first line segment, and going from the first position to the first straight line, and
detecting an eye gaze, by an eye gaze detector processor or circuit, based on calculating, by a calculator, the first distance where a ratio of a length of the second line segment to a length of the first line segment, and a ratio of the first distance to a distance between the third position and the fourth position become equal.

* * * * *